(12) United States Patent
Samaritoni et al.

(10) Patent No.: US 7,375,122 B2
(45) Date of Patent: May 20, 2008

(54) COMPOUNDS USEFUL AS PESTICIDES

(75) Inventors: Jack Geno Samaritoni, Avon, IN (US); David Anthony Demeter, Fishers, IN (US); Zoltan Laszlo Benko, Indianapolis, IN (US); James Michael Gifford, Lebanon, IN (US); Paul Allen Neese, Tucson, AZ (US); Leonard Paul Dintenfass, Indianapolis, IN (US); Carrie Lynn Rau Schmidt, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 559 days.

(21) Appl. No.: 10/535,513

(22) PCT Filed: Dec. 19, 2003

(86) PCT No.: PCT/US03/40703

§ 371 (c)(1), (2), (4) Date: May 18, 2005

(87) PCT Pub. No.: WO2004/058714

PCT Pub. Date: Jul. 15, 2004

(65) Prior Publication Data

US 2006/0040902 A1    Feb. 23, 2006

Related U.S. Application Data

(60) Provisional application No. 60/435,929, filed on Dec. 20, 2002.

(51) Int. Cl.
- *A61K 31/44* (2006.01)
- *C07D 213/02* (2006.01)
- *C07D 401/06* (2006.01)
- *A01N 43/36* (2006.01)
- *A01N 43/40* (2006.01)

(52) U.S. Cl. ............... 514/357; 546/268.1; 546/268.4; 546/272.7; 546/275.1; 546/329; 546/334; 514/336; 514/341; 504/209; 504/244; 504/283

(58) Field of Classification Search ............. 546/268.1, 546/268.4, 272.7, 275.1, 329, 334; 514/336, 514/341, 357; 504/209, 244, 283
See application file for complete search history.

(56) References Cited

U.S. PATENT DOCUMENTS

| | | | | |
|---|---|---|---|---|
| 5,438,065 A | * | 8/1995 | Uneme et al. | 514/353 |
| 6,124,297 A | * | 9/2000 | Minamida et al. | 514/252.02 |

* cited by examiner

*Primary Examiner*—Golam M. M. Shameem
(74) *Attorney, Agent, or Firm*—Ronald Maciak; Carl Corvin

(57) ABSTRACT

Compounds useful to control pests are provided.

6 Claims, No Drawings

COMPOUNDS USEFUL AS PESTICIDES

PRIORITY

This application claims priority from U.S. provisional application 60/435,929 which was filed on Dec. 20, 2002.

FIELD OF THE INVENTION

This invention provides compounds that are useful as pesticides.

BACKGROUND OF THE INVENTION

There is an acute need for new pesticides. For example, insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore, a need exists for new insecticides and acaricides, and particularly for compounds that have new or atypical modes of action.

DETAILED DESCRIPTION OF THE INVENTION

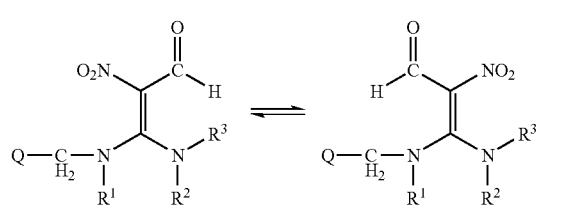

Figure One

In Figure One Q, $R^1$, $R^2$, and $R^3$ have the following meanings.

Q can be any five or six membered carbocyclic or heterocyclic ring, such as, phenyl, pyridyl, pyridazinyl, pyrimidinyl, pyrazinyl, pyrrolyl, pyrazolyl, imidazolyl, thienyl, furanyl, thiazolyl, isothiazolyl, oxazolyl, and isoxazolyl, and including reduced forms of the heterocyclic rings such as tetrahydrofuranyl.

$R^1$, $R^2$, and $R^3$ each independently can be:
 (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, or HC(=NH)—;
 (b) a $C_{3-10}$, cycloalkyl, or cycloalkenyl;
 (c) an aryl, heterocyclyl, aryloxy, heterocyclyloxy, arylthio, heterocyclylthio, arylamino, or heterocyclylamino; or
 (d) a hydro, hydroxy, mercapto, amino, cyano, formyl, nitro, halo, or aminocarbonyl.

Additionally, $R^1$ and $R^2$ can be joined together to form a ring, either directly with a bond between them, or indirectly through one or two linkage atoms, where such linkage atoms are either carbon, nitrogen, oxygen, or sulfur.

Each member of Q, each member of $R^1$, $R^2$, and $R^3$, and any of the linkage atoms, which may have a hydrogen atom in a certain position, may instead of having such hydrogen atom, have a:
 (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, HC(=NH)—, dialkylphosphonyl, or dialkylphosphatyl;
 (b) a $C_{3-10}$, cycloalkyl, or cycloalkenyl;
 (c) an aryl, heterocyclyl, aryloxy, heterocyclyloxy, arylthio, heterocyclylthio, arylamino, or heterocyclylamino; or
 (d) a hydro, hydroxy, mercapto, amino, cyano, formyl, nitro, halo, or aminocarbonyl;

in such position, provided that these substituents are sterically compatible and the rules of chemical bonding and strain energy are satisfied. Figure One is a generic structure. It should be noted that this generic structure can represent, depending on the substituents used, two generic isomers due to the presence of the double bond. These two generic isomers can exist in a dynamic equilibrium with each other and so interconvert through tautomeric or canonical forms by free rotation around the relevant bond. This invention comprises all such interconverting isomers and purified derivatives thereof. The nature of tautomeric and canonical forms is understood to be as described in "Advanced Organic Chemistry: Reactions, Mechanisms and Structure", 4$^{th}$ edition, J. March ed., John Wiley and Sons, New York, 1992.

The term "aryl" means a monovalent radical derived by loss of hydrogen from an aromatic hydrocarbon. The term heteroaryl means a monovalent radical derived by loss of a hydrogen from a ring structure, where such ring structure contains one or more nitrogen, oxygen, or sulfur atoms. Examples of aryls and heteroaryls include, but are not limited to, phenyl, naphthyl, pyridyl, pyridazinyl, pyrimidinyl, pyrazinyl, pyrrolyl, pyrazolyl, imidazolyl, thienyl, furanyl, thiazolyl, isothiazolyl, oxazolyl, and isoxazolyl, and included are reduced forms of the heteroaryls such as tetrahydrofuranyl.

All salts and esters of these compounds are contemplated as part of this invention.

The compounds of the invention are useful for the control of pests such as, insects and mites. Therefore, the present invention also is directed to a method for inhibiting an insect or mite which comprises applying to a locus of the insect or mite an insect- or mite-inhibiting amount of a compound of this invention. In particular, these compounds control insects in the order Homoptera, including the families Aphididae (aphids), Aleyrodidae (whiteflies), Delphacidae (planthoppers), and Cicadellidae (leafhoppers). They also control insects in the order Coleoptera (beetles), including the family Chrysomelidae (leaf beetles). Also, they control lepidopterans such as tobacco budworm and cabbage looper. In particular, other representative pests which may be controlled by the method of this invention include members of the Arthropoda, including mites of the suborders Mesostigmata, Sarcoptiformes, Trombidiformes and Onchychopalpida; sucking and biting lice of the orders Anoplura and Mallophaga: ticks of the families Ixodidae and Argasidae: fleas of the families Pulicidae, Ceratophyllidae, and others; Cimex and other Hemiptera; Triatoma and other Heteroptera: and myiasis-related fly larvae and blood sucking adults (including mosquitoes) of the suborders Brachycera, Cyclorrhapha and Nematocera. Representative also are helminths included in the Nematoda (Strongylida, including but not limited to Strongyloidea, Ancylostomatoidea, Trichostrongyloidea and Metastrongyloidea; Ascarida, Ascarisl; Filarlina, such as but not limited to *Onchocerca* and *Dirofilaria*; Rhabditida; and Trichinellida); Cestoidea, especially Cyclophyllidea, and Trematoda, including Strigeatoidea such as *Schistosoma*; Echinostomida such as *Fasciola*; and Plagiorchiida such as *Paraqonimus*. Other pests which may be controlled by compounds of this invention Acanthocephala such as *Macracanthorhynchus, Onicola* or *Moniliformis*, and Pentastomida, especially *Linguatula*; and Protozoa, especially Coccidia such as *Elmeria* and *Plasmodium*, Piroplasmea such as *Babesia*; Toxoplasmea such as *Trypanosoma*, Trichomonadidae such as *Trichomonas* and Entamoebidae such as *Entamoeba*. Illustrative of specific pests of various animals which may be controlled by the method of this invention include arthropods such as mites (mesostigmatids, itch. mange, scabies. chiggers), ticks (soft-bodied and hard-bodied), lice (sucking, biting), fleas (dog flea, cat flea, oriental rat flea), true bugs (bed bugs, kissing bugs), bloodsucking adult flies (horn fly, horse fly, stable fly. black fly, deer fly, louse fly, tsetse fly, punkies, mosquitoes), and parasitic fly maggots (bot fly, blow fly, screwworm, cattle grub, fleeceworm); helminths such as nematodes (threadworm, lungworm, hookworm, whipworm, nodular worm, stomach worm, round worm, pinworm, heartworm), cestodes (tapeworms) and trematodes (liver fluke, blood fluke); protozoa such as coccidia, trypanosomes, trichomonads, amoebas and plasmodia; acanthocephalans such as thorny-headed worms; and pentastomids such as tongueworms.

The compounds are useful for reducing populations of insects and mites and are useful in a method of inhibiting an insect or mite population which comprises applying to a locus of the insect or mite an effective insect- or mite-inactivating amount of a compound of this invention.

The "locus" of insects or mites is a term used herein to refer to the environment in which the insects or mites live or where their eggs are present, including the air surrounding them, the food they eat, or objects or materials which they contact. For example, plant-ingesting insects or mites can be controlled by applying the active compound to plant parts that the insects or mites eat, particularly the foliage. Soil-inhabiting insects such as termites can be controlled by applying the active compound to the soil that the insects move through. Insects such as fleas that infest animals can be controlled by applying the active compound to the animal that is infested. Oral administration of the compounds of this invention may be performed by mixing the compound in the animal's feed or drinking water, vitamin or mineral supplement, or by administering oral dosage forms such as drenches, tablets, bolus, salt block or capsules.

It is contemplated that the compounds might also be useful to protect textiles, paper, stored grain, or seeds by applying an active compound to such substance.

The term "inhibiting an insect or mite" refers to a decrease in the numbers of living insects or mites, or a decrease in the number of viable insect or mite eggs. The extent of reduction accomplished by a compound depends, of course, upon the application rate of the compound, the particular compound used, and the target insect or mite species. At least an inactivating amount should be used.

The terms "insect-inactivating amount" and "mite-inactivating amount" are used to describe the amount, which is sufficient to cause a measurable reduction in the treated insect or mite, population. Generally an amount in the range from about 1 to about 1000 ppm by weight active compound is used. In another embodiment, the present invention is directed to a method for inhibiting a mite or insect which comprises applying to a plant an effective mite- or insect-inactivating amount of a compound of this invention.

The compounds of this invention are applied in the form of compositions which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an Inert carrier, and surfactants. The concentration of the active compound is usually from about 10% to about 90% by weight. The inert carrier is usually chosen from among the attapulgite clays, the montmorillonite clays, the diatomaceous earths, or the purified silicates.

Effective surfactants, comprising from about 0.5% to about 10% of the wettable powder, are found among the sulfonated lignins, the condensed naphthalenesulfonates, the naphthalenesulfonates, the alkylbenzene-sulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines, crop oil concentrates containing high molecular weight paraffinic oils and blends of surfactants with mineral and vegetable oils.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects, mites, and aphids is not critical and can readily be determined by those skilled in the art in view of the examples above. In general, concentrations of from-10 ppm to 5000 ppm by weight of compound are expected to provide good control. With many of the compounds, concentrations of from 100 to 1500 ppm will suffice.

The locus to which a compound is applied can be any locus inhabited by an insect or arachnid, for example, vegetable crops, fruit and nut trees, grape vines, and ornamental plants.

Because of the unique ability of mite eggs to resist toxicant action, repeated applications may be desirable to control newly emerged larvae, as is true of other known acaricides.

In addition to being effective against mites, aphids, and insects when applied to foliage, compounds of this invention have systemic activity. Accordingly, another aspect of the invention is a method of protecting a plant from insects which comprises treating plant seed prior to planting it, treating soil where plant seed is to be planted, or treating soil at the roots of a plant after it is planted, with an effective amount of a compound of this invention.

The action of the inventive compounds can be broadened by adding other, for example insecticidally, acaricidally, and/or nematocidally active, ingredients. For example, one or more of the following compounds can suitably be combined with the compounds of the invention:

(1) organophosphorus compounds such as acephate, azinphosmethyl, cadusafos, chlorethoxyfos, chlorpyrifos, coumaphos, dematon, demeton-S-methyl, diazinon, dichlorvos, dimethoate, EPN, erthoate, ethoprophos, etrimfos, fenamiphos, fenitrothion, fensulfothion, fenthion, fonofos, formothion, fosthiazate, heptenophos, malathion, methamidophos, methyl parathion, mevinphos, monocrotophos, parathion, phorate, phosalone, phosmet, phosphamidon, phosphocarb, phoxim, profenofos, propaphos, propetamphos, prothiofos, pyrimiphos-methyl, pyrimiphos-ethyl, quinalphos, sulprofos; tebupirimphos, temephos, terbufos, tetrachlorvinphos, thiafenox, thiometon, triazophos, and trichlorphon;

(2) carbamates such as aldicarb, bendiocarb, benfuracarb, bensultap, BPMC, butoxycarbocim, carbaryl, carbofuran, carbosulfan, cloethocarb, ethiofencarb, fenobucarb, furathiocarb, methiocarb, isoprocarb, methomyl, oxamyl, pirimicarb, promecarb, propoxur, thiodicarb, and thiofurox;

(3) pyrethroids such as acrinathrin, allethrin, beta-cyfluthrin, bifenthrin, bioresmethrin, cyfluthrin; cyhalothrin; lambda-cyhalothrin; gamma-cyhalothrin, cypermethrin; alpha-cypermethrin; zeta-cypermethrin; deltamethrin, esfenvalerate, fenvalerate, fenfluthrin, fenpropathrin, flucythrinate, flumethrin, fluvalinate, tau-fluvalinate, halfenprox, permethrin, protrifenbute, resmethrin, silafluofen, tefluthrin, tetramethrin, tralomethrin, fish safe pyrethroids for example ethofenprox, natural pyrethrin, tetramethrin, s-bioallethrin, fenfluthrin and prallethrin;

(4) acylureas, other types of insect growth regulators and insect hormone analogs such as buprofezin, chromfenozide, chlorfluazuron, diflubenzuron, fenoxycarb, flufenoxuron, halofenozide, hexaflumuron, hydroprene, leufenuron, methoprene, methoxyfenozide, novaluron, pyriproxyfen, teflubenzuron and tebufenozide, N-[3,5-dichloro-2-fluoro-4-(1,1,2,3,3,3-hexafluoropropoxy)phenyl]-N'(2,6-difluorobenzoyl) urea;

(5) neonicotnioids and other nicotinics such as acetamiprid, AKD-1022, cartap, TI-435, clothianidin, MTI-446, dinotefuran, imidacloprid, nicotine, nitenpyram, thiamethoxam, thiacloprid;

(6) macrolides such as avermectins, milbemycins, or spinosyns for example such as abamectin, ivermectin, milbemycin, emamectin benzoate and spinosad; and (7) other insecticidal, acaricidal, molluscicidal and nematocidal compounds or actives such as aldrin, amitraz, azadirachtin, azocyclotin. bifenazate, bromopropylate, chlordimeform, chlorfenapyr, chlorfentezine, chlorobenzilate, chlordane, cyhexatin, cyromazin, DDT, dicofol, dieldrin, DNOC, endosulfan, ethoxazole, fenazaquin, fenbutatin oxide, fenproximate, beta-fenpyroximate, fipronil, flubenzimine, hexythiazox, IKI-220, indoxacarb, lindane, methiocarb, metaldehyde, methoxychlor, neem, petroleum and vegetable oils, pyridaben, pymetrozine, pyrimidifen, rotenone, S-1812, S-9539, spirodiclofen, sulfur, tebufenpyrad, tetradifon, triazamate, an insect-active extract from a plant; a preparation containing insect-active nematodes, a preparation obtainable from Bacillus subtilis, Bacillus thuringiensis, a nuclear polyhedrosis virus, or other like organism genetically modified or native, as well as synergists such as piperonyl butoxide, sesamax, safroxan and dodecyl imidazole, and phagostimulants such as cucurbitacin, sugars and Coax.

EXAMPLES

These examples are provided to further illustrate the invention. They are not meant to be construed as limiting the invention.

Example One

Preparation of Compound One

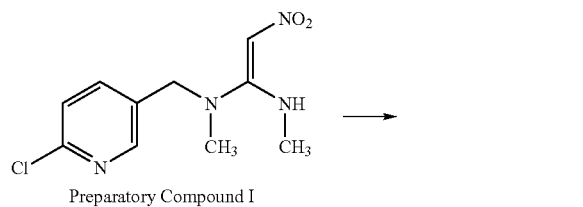

Preparatory Compound I

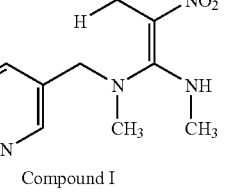

Preparatory Compound II

A solution of 6.0 g (23.4 mmol) of Preparatory Compound I (J. Pesticide Sci., 18, 31-40, 1983) in 35 mL of dimethylformamide dimethylacetal was heated at 85-90° C. for 3 hours and was then allowed to cool to room temperature, which was about 22° C. The volatiles were removed in vacuo and the resulting oil was triturated under ethyl ether and ethyl acetate with a small amount of methanol to give 2.2 g (30%) of Preparatory Compound II as a tan solid.

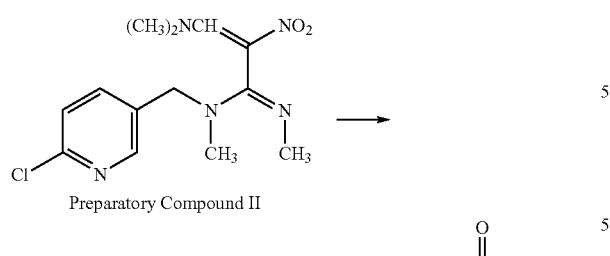

Preparatory Compound II

Compound I

A solution of 130 mg (0.42 mmol) of Preparatory Compound II in 4 mL of concentrated ammonium hydroxide was stirred at room temperature, which was about 22° C., for 20 hours. The resulting mixture was concentrated to a residue which was chromatographed on silica gel (230-400 mesh) eluting with 95/5 dichloromethane/methanol to give 80 mg (67%) of Compound One.

Example Two

Alternative Preparation of Compound One

A solution of 200 mg (0.641 mmol) of Preparatory Compound II in 3 mL of methanol was treated with 0.32 mL (0.64 mmol) of 2.0 N sodium hydroxide. This mixture was then heated at reflux for 2.5 hours, followed by cooling to about 22° C. The resulting portion was then concentrated to an oil, which was then treated with 0.64 mL (0.64 mmol) of 1.0 N hydrochloric acid. The resulting mixture was then extracted three times with dichloromethane, the combined extracts were then dried over sodium sulfate and were then concentrated to give 190 mg of a residue which was chromatographed on silica gel to give 130 mg (71%) of Compound One, mp 100-103° C.

Example Three

Preparation of Compounds One and Two

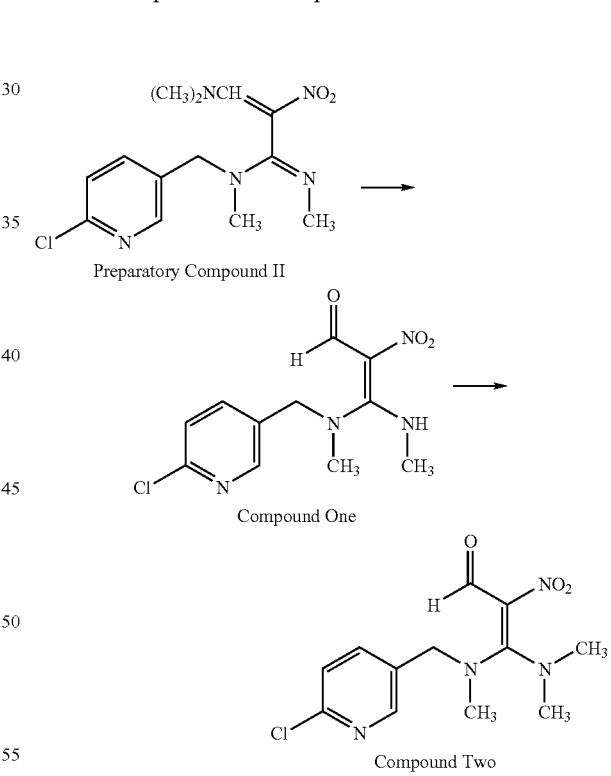

To a solution of 18.9 mg (0.822 mmol) of sodium metal in 3 mL of absolute ethanol was added in one portion 200 mg (0.641 mmol) of Preparatory Compound II. The contents were stirred at room temperature, which was about 22° C., for 3 hours. The solution was cooled in ice and was treated with 0.13 mL (296 mg, 2.09 mmol)) of methyl iodide in 1.5 mL of ethanol. After stirring overnight at room temperature, which was about 22° C., the mixture was concentrated and the residue was partitioned between dichloromethane and water. Hydrochloric acid (1.0 N, 0.64 mL) was added followed by sodium bicarbonate to give a pH of 10-11. The mixture was extracted three times with dichloromethane, the combined extracts were dried over magnesium sulfate and were concentrated to give 160 mg of an oil which was chromatographed on silica gel using 95/5 dichloromethane/ methanol as eluant to give 130 mg (71%) of Compound One and 10 mg (5%) of Compound Two, mp 163-166° C.

Example Four

Preparation of Compound Three

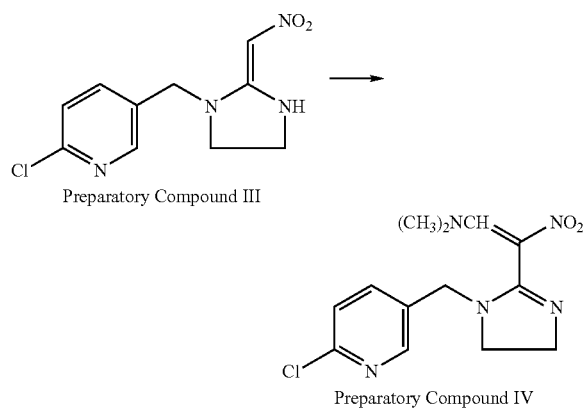

A solution of 255 mg (1.00 mmol) of Preparatory Compound III (EP 163855 A1) and 238 mg (2.00 mmol) of dimethylformamide dimethylacetal in 3 mL of dry toluene was heated at 100-110° C. for 6 hours and was then allowed to cool to room temperature, which was about 22° C. The toluene was removed in vacuo and the resulting solid was triturated under ethyl ether to afford 272 mg (88%) of Preparatory Compound IV as a yellow solid, mp 115-123° C.

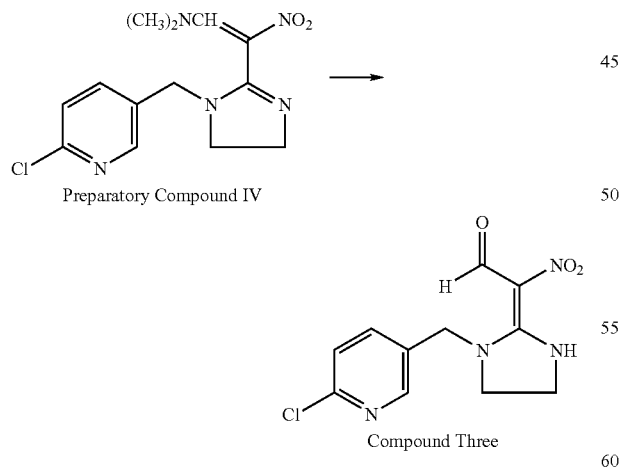

A solution of 161 mg (0.521 mmol) of Preparatory Compound IV and 0.286 mL (0.573 mmol) of 2.0 N sodium hydroxide in 3 mL of methanol was stirred at room temperature, which was about 22° C., for 7 hours and was then cooled in ice. The resulting solution was then treated with 0.572 mL (0.572 mmol) of 1.0 N hydrochloric acid. The precipitate was collected to afford 90 mg (61%) of Compound Three, mp 196-197° C. (dec).

Example Five

Testing with Cotton Aphid (*Aphis gossypll*)

Alcala cotton plants were grown from seed in 7-cm pots under greenhouse conditions until they reached 35 to 40 cm in height; approximately four weeks old with 5 to 6 true leaves. The plants were then stripped of all foliage except for the two uppermost true leaves. Two days prior to application, heavily infested leaf sections from a cotton aphid colony were cut and placed on each untreated leaf surface. Over the two days, all stages of the aphids abandon the excised host material and migrate to the succulent growth, predominantly the lower surface of the leaves. Plants were checked prior to application for even infestation levels. Treatments consisted of 4 replicates (plants) each with 2 leaves per plant.

Formulation of technical compound was in a solvent solution. For the top rate of each compound, 20 milligrams of technical material was dissolved in 2 milliliters (ml) of a 9:1 mixture of acetone:ethanol solvent. Once dissolved, an additional 18-ml of the solvent mix was added to yield a 1 mg/ml spray solution. Additional rates were then prepared by serial dilution.

Application was made by an automated tracksprayer (RC-Insecticide #1, Serial MS-9'-002, MANDEL Scientific Company Ltd.) equipped with a single TX6 SS hollow cone nozzle to simulate an over-the-top application by a boom sprayer. Spray pressure was set at 50 PSI, and the nozzle head was set approximately 40 cm above the leaf surface (depending on the leaf position it ranged from 35-45 cm). Track velocity and all other settings were calibrated to deliver approximately 200 L/ha. After application and drying, the plants were transferred and kept in controlled environment until assessment.

Assessment of compound efficacy is evaluated by counting all living non-winged stage aphids infesting each replicate using a dissecting microscope.

The compounds tested in this manner were as follows

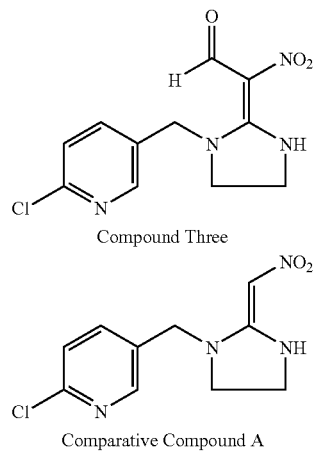

The results indicate that the LC90 in grams per hectare for Compound Three was less than 0.78 grams per hectare, whereas, the LC90 for Comparative Compound A was 9.1 grams per hectare. This means nearly 11.7 times more Comparative Compound A was needed to reach the LC90 level than Compound Three.

Example Six

Testing with Sweetpotato Whitefly, *Bemisia tabaci*

Greenhouse-grown cotton plants (ca. five weeks old, grown in 7×7 cm pots containing ca. 231 cm³ of potting soil mixture) were prepared for whitefly infestation by removing all foliage except the first or second pair of fully expanded true leaves. These plants are then moved into the whitefly colony room of the insectary (temperature maintained at 27° C.), where they are surrounded by cotton or velvetleaf plants infested with all life stages of *B. tabaci*. Initial movement of *B. tabaci* adults onto the prepared cotton plants is encouraged by gently shaking the foliage of the surrounding infested cotton and velvetleaf foliage using a 1.5-meter long willow branch. The prepared plants are left in place within the whitefly colony, where they are exposed to adult female *B. tabaci* oviposition for ca. 48 hours.

At the end of the oviposition exposure period, adult whiteflies are dislodged from the prepared plants by passing compressed air just above the leaves while the leaves are gently disturbed by hand for ca. 15 seconds. The prepared plants, which are now infested with eggs of *B. tabaci*, are removed from the insectary and any remaining adults are removed from the foliage with a hand-held vacuum fitted with a cage to trap insects. Infested plants are then selected at random and arranged into treatment groups of two or three plants each. Leaves of plants to receive different treatments are separated by a distance of at least 5 cm.

Compounds are applied within 24 hours of removing cotton plants from exposure to oviposition within the *B. tabaci* colony. Immediately after application, plants are moved to a holding room with a temperature of 30° C. and relative humidity of ca. 60%. Compound efficacy was observed by an assessment at 13 days after application. At this evaluation time, whitefly nymphs that have successfully developed to the third and fourth nymphal stadia can be easily seen on the underside of each cotton leaf with the aid of an illuminated magnifying lens (equipped with a circular fluorescent tube).

Track sprayer application is designed to simulate field application of compounds. As in field applications, the equipment is first calibrated to deliver the desired spray volume, in liters/ha. Next, volumes of spray solution containing known amounts of test compound are prepared, so that when applied at the known liters/ha spray volume, the desired g [AI]/ha rate will be delivered.

The compounds tested in this manner were as follows.

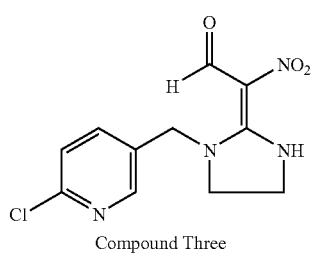

Compound Three

-continued

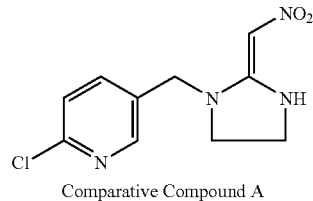

Comparative Compound A

The results indicate that the LC90 in grams per hectare for Compound Three was less than 2.52 grams per hectare, whereas, the L90 for Comparative Compound A was 6.66 grams per hectare. This means nearly 2.7 times more Comparative Compound A was needed to reach the LC90 level than Compound Three.

Example Seven

Testing with Cat Flea (*Cntenocephalides felis*)

Media is prepared by mixing 1 part dried bovine blood, 4 parts ground dog food pellets, and 95 parts clean sand. Compounds are dissolved in acetone and further diluted in acetone to yield the required range of concentrations. The acetone solutions are applied to measured amounts of media in small dishes. Final concentrations are expressed as micrograms of compound per gram of media. After the acetone has dried, the treated media is dispensed into small glass vials and infested with 5 to 10 cat flea (*Cntenocephalides fells*) eggs. The vials are loosely capped and held under controlled conditions for five weeks. Activity is assessed based on the average number of adult cat fleas present in the treated vials compared to the average number of adult cat fleas in the media The compounds tested in this manner were as follows.

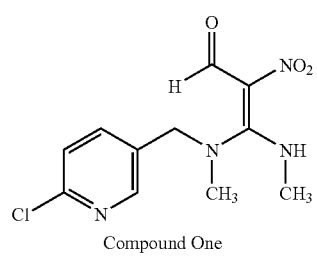

Compound One

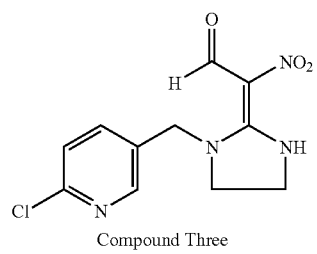

Compound Three

The results indicate that Compound One showed 100% control of cat fleas at the 0.1 µg/g rate, whereas Compound Three showed 96% control of cat fleas at the 0.1 µg/g rate, and 81% at the 0.01 µg/g rate.

We claim:

1. A compound according to

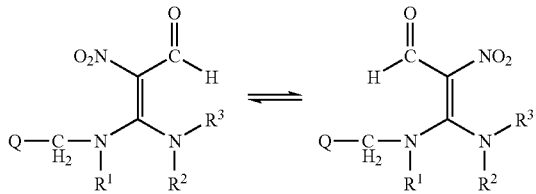

Figure One wherein

Q can be any five or six membered carbocyclic or heterocyclic ring, $R^1$, $R^2$, and $R^3$ each independently can be (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, HC(=NH)—, (b) a $C_{3-10}$, cycloalkyl, or cycloalkenyl, (c) an aryl, heterocyclyl, aryloxy, heterocyclyloxy, arylthio, heterocyclylthio, arylamino, or heterocyclylamino, or (d) a hydro, hydroxy, mercapto, amino, cyano, formyl, nitro, halo, or aminocarbonyl, $R^1$ and $R^2$ can be joined together to form a ring, either directly with a bond between them, or indirectly through one or two linkage atoms, where such linkage atoms are either carbon, nitrogen, oxygen, or sulfur, and wherein each member of Q, each member of $R^1$, $R^2$, and $R^3$, and any of the linkage atoms, which may have a hydrogen atom in a certain position, may instead of having such hydrogen atom, have a (a) a $C_{1-10}$, branched or unbranched, alkyl, alkoxy, alkenyl, alkynyl, alkylthio, alkylsulfinyl, alkylsulfonyl, alkylcarbonyl, alkylcarbonothioyl, alkoxycarbonyl, alkylthiocarbonyl, alkoxycarbonothioyl, alkylthiocarbonothioyl, HC(=NH)—, dialkylphosphonyl, or dialkylphosphatyl, (b) a $C_{3-10}$, cycloalkyl, or cycloalkenyl, (c) an aryl, heterocyclyl, aryloxy, heterocyclyloxy, arylthio, heterocyclylthio, arylamino, or heterocyclylamino, or (d) a hydro, hydroxy, mercapto, amino, cyano, formyl, nitro, halo, or aminocarbonyl, in such position.

2. A composition comprising a compound according to claim 1 and at least one other active compound where such active compound is at least insecticidally, acaricidally, or nematocidally active.

3. A process of applying a compound according to claim 1, or a composition according to claim 2, to a locus in an amount effective to control pests.

4. A process of applying a compound according to claim 1, or a composition according to claim 2, to a locus in an amount effective to control insects or mites.

5. A process of topically applying a compound according to claim 1, or a composition according to claim 2, to an animal in an amount effective to control fleas.

6. A process of orally administering a compound according to claim 1, or a composition according to claim 2, to an animal in an amount effective to control fleas.

* * * * *